US009343379B2

(12) United States Patent
Libbert et al.

(10) Patent No.: US 9,343,379 B2
(45) Date of Patent: May 17, 2016

(54) METHOD TO DELINEATE CRYSTAL RELATED DEFECTS

(75) Inventors: Jeffrey L. Libbert, O'Fallon, MO (US); Lu Fei, St. Louis, MO (US)

(73) Assignee: SunEdison Semiconductor Limited, Singapore (SG)

( * ) Notice: Subject to any disclaimer, the term of this patent is extended or adjusted under 35 U.S.C. 154(b) by 0 days.

(21) Appl. No.: 14/350,899

(22) PCT Filed: Oct. 4, 2011

(86) PCT No.: PCT/US2011/056428
§ 371 (c)(1),
(2), (4) Date: Jul. 17, 2014

(87) PCT Pub. No.: WO2013/055368
PCT Pub. Date: Apr. 18, 2013

(65) Prior Publication Data
US 2014/0327112 A1    Nov. 6, 2014

(51) Int. Cl.
*H01L 21/66* (2006.01)
*G01N 1/32* (2006.01)
*H01L 29/34* (2006.01)

(52) U.S. Cl.
CPC *H01L 22/12* (2013.01); *G01N 1/32* (2013.01); *H01L 29/34* (2013.01)

(58) Field of Classification Search
CPC combination set(s) only.
See application file for complete search history.

(56) References Cited

U.S. PATENT DOCUMENTS

| 6,284,039 | B1 | 9/2001 | Mule'Stagno et al. |
| 6,548,886 | B1 * | 4/2003 | Ikari et al. ............ 257/610 |
| 2002/0174828 | A1 | 11/2002 | Vasat et al. |
| 2004/0060899 | A1 | 4/2004 | Waldhauer et al. |
| 2005/0035349 | A1 | 2/2005 | Umeno et al. |

FOREIGN PATENT DOCUMENTS

JP          200100730 A     4/2000

OTHER PUBLICATIONS

Characterization of Crystal Quality by Delineation of COP and the Impact on the Silicon Wafer Surface, Suhren et al, 1996, Electrochemical Socirty Proceedings, vol. 96-13, pp. 117-131.*
International Search Report and Written Opinion of the International Searching Authority regarding PCT/US2011/056428 mailed on Jun. 14, 2012; 11 pgs.

* cited by examiner

*Primary Examiner* — Fernando L Toledo
*Assistant Examiner* — Valerie N Newton
(74) *Attorney, Agent, or Firm* — Armstrong Teasdale LLP

(57) ABSTRACT

This invention generally relates to a process for detecting grown-in-defects in a semiconductor silicon substrate. The process includes contacting a surface of the semiconductor silicon substrate with a gaseous acid in a reducing atmosphere at a temperature and duration sufficient to grow grown-in-defects disposed in the semiconductor silicon substrate to a size capable of being detected by an optical detection device.

11 Claims, 7 Drawing Sheets

METHOD TO DELINEATE CRYSTAL RELATED DEFECTS

CROSS REFERENCE TO RELATED APPLICATION

This application claims priority of U.S. PCT Application No. PCT/US2011/056428, published as WO 2013/055368 and filed on Oct. 14, 2011 which is hereby incorporated by reference in its entirety.

FIELD OF THE INVENTION

BACKGROUND OF THE INVENTION

Single crystal silicon, which is the starting material for most processes for the fabrication of semiconductor electronic components, is commonly prepared by the so-called Czochralski ("Cz") method. In this method, polycrystalline silicon ("polysilicon") is charged to a crucible and melted, a seed crystal is brought into contact with the molten silicon, and then a single crystal ingot is grown by slow extraction. After formation of a neck is complete, the diameter of the crystal is enlarged by decreasing the pulling rate and/or the melt temperature until the desired or target diameter is reached. The cylindrical main body of the crystal, which has an approximately constant diameter, is then grown by controlling the pull rate and the melt temperature while compensating for the decreasing melt level. Near the end of the growth process, but before the crucible is emptied of molten silicon, the crystal diameter must be reduced gradually to form an end-cone. Typically, the end-cone is formed by increasing the crystal pull rate and heat supplied to the crucible. When the diameter becomes small enough, the crystal is then separated from the melt.

Czochralski-grown ingots are then cut to eliminate the generally cone-shaped ends, their central cylindrical portion may be segmented into a plurality of segments, and each segment sliced into a plurality of wafers. Each wafer is finished, e.g., by grinding and polishing, so that its two opposite faces are flat, and then may be etched, e.g., by chemical etching steps, so that dust, residual particles, and zones damaged during the preceding material-removal steps are eliminated.

In recent years, it has been recognized that Czochralski-grown silicon can host a number of different defects associated with this growth process. Among these defects are vacancy agglomerations of various sizes, interstitial agglomerations of various sizes, and oxygen precipitates with a size that depends on the specific crystal process used. While the densities of these defects are typically relatively low, these defects can severely impact the yield potential of the material in the production of complex and highly integrated circuits. As a result, accurate and efficient detection of such defects is critical for purposes of both quality assurance and process control.

Vacancy-type defects are recognized to be the origin of such observable crystal defects, for example, D-defects. Vacancy-type defects are often referred to according to one or more of the test methods generally used to identify such defects including but not limited to Flow Pattern Defects (FPDs), Gate Oxide Integrity (GOI) Defects, Crystal Originated Particle (COP) Defects, crystal originated Light Point Defects (LPDs), Direct Surface Oxidation Defects (also referred to as DSOD) as well as certain classes of bulk defects observed by infrared light scattering techniques such as Scanning Infrared Microscopy and Laser Scanning Tomography defects (LSTDs). Also present in regions of excess vacancies are defects which act as the nuclei for ring oxidation induced stacking faults (OISF). It is speculated that this particular defect is a high temperature nucleated oxygen agglomerate catalyzed by the presence of excess vacancies.

Defects relating to self-interstitials are less well studied. They are generally regarded as being low densities of interstitial-type dislocation loops or networks. Such defects are not responsible for gate oxide integrity failures, an important wafer performance criterion, but they are widely recognized to be the cause of other types of device failures usually associated with current leakage problems. Since many defects are relatively small and can be of very low density, it can be a laborious process to determine if any of the possible crystal related defects are present at a given place in a crystal or on a given wafer. More specifically, although large vacancy agglomerations can be detected via surface inspection of a polished wafer, very small vacancy agglomerations, oxygen precipitates and interstitial agglomerates are not detected easily in polished wafer form. In such cases, laborious tests, such as the FPD, DSOD, LSTD and/or thermal cycles in combination with cleaving and etching the exposed surface are required to delineate and count defect densities. In addition, most of these methods further require manual inspections and counting procedures to quantify the densities.

SUMMARY OF THE INVENTION

Briefly, therefore, the present invention is directed to a method for detecting grown-in-defects in a surface of a semiconductor substrate. The method comprises exposing the surface of the semiconductor substrate to a reducing atmosphere comprising gaseous etchant selected from the group consisting of hydrogen chloride, hydrogen bromide, hydrogen iodide, and combinations thereof at a temperature and duration sufficient to etch the surface of the semiconductor silicon substrate and delineate grown-in-defects disposed in the semiconductor silicon substrate and scanning the surface of the semiconductor silicon substrate having delineated grown-in-defects thereon with an optical detection device.

The invention is further directed to a semiconductor substrate comprising grown-in-defects. The semiconductor substrate is formed by a process comprising exposing the surface of the semiconductor substrate to a reducing atmosphere comprising gaseous hydrogen chloride at a temperature and duration sufficient to etch the surface of the semiconductor silicon substrate and delineate grown-in-defects disposed in the semiconductor silicon substrate.

The invention is still further directed to method of sorting a plurality of semiconductor wafers. The method comprises exposing the plurality of semiconductor wafers to a reducing atmosphere comprising gaseous etchant selected from the group consisting of hydrogen chloride, hydrogen bromide, hydrogen iodide, and combinations thereof at a temperature and duration sufficient to etch the surface of the semiconductor silicon substrate and delineate grown-in-defects disposed in the semiconductor silicon substrate, scanning the surface of the wafers with an optical detection device for the delineated grown-in-defects, and sorting the wafers based on the type, concentration, and size of the defects detected.

Other objects and features of this invention will be in part apparent and in part pointed out hereinafter.

BRIEF DESCRIPTION OF THE DRAWINGS

FIG. 1B shows oxygen precipitates have been delineated by the process of the present invention.

DETAILED DESCRIPTION OF THE EMBODIMENT(S) OF THE INVENTION

Figure 1A:
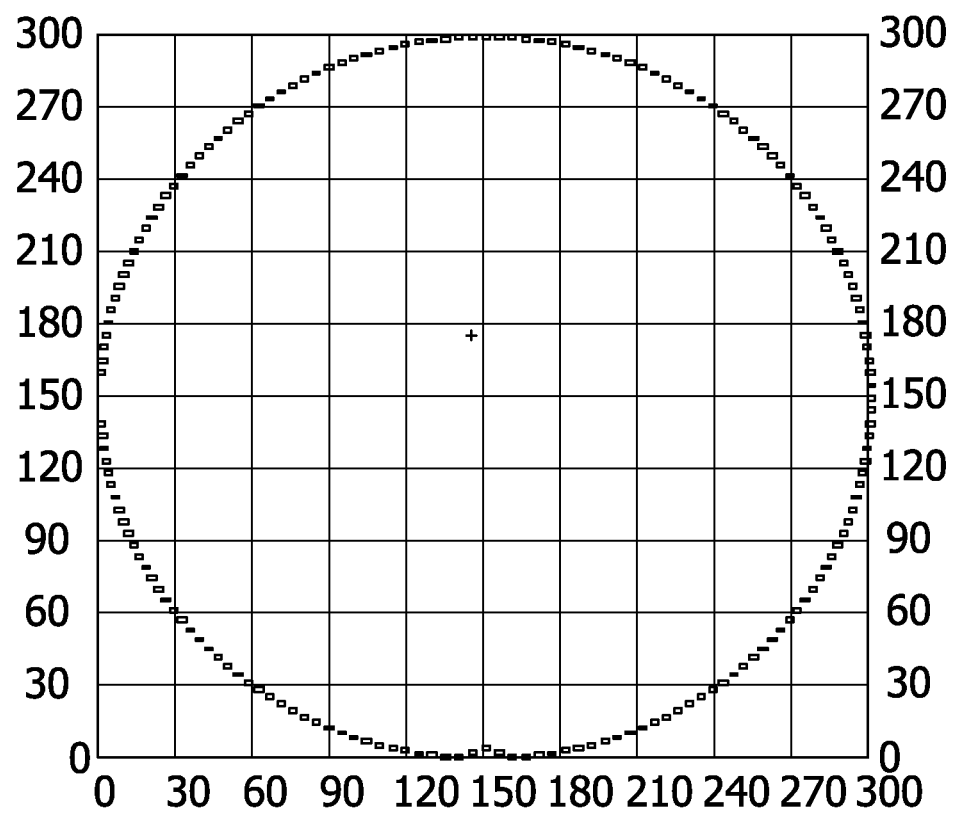
FIGS. 1A and 1B are illustrations of oxygen precipitates on the surface of a wafer before an HCl etch of the present invention (FIG. 1A) and after an HCl etch of the present invention (FIG. 1B).

The present invention generally relates to a process for evaluating the quality of a semiconductor substrate. More particularly, the present invention relates to an improved process for delineating and counting crystal related defects on a semiconductor surface. Even more particularly, the process of the present invention is directed to delineating grown-in-defects in a semiconductor substrate. By "grown-in-defects" it is meant defects that originate from the crystal growth method, e.g., a Czochralski crystal growing method. Exemplary grown-in-defects include COPs, oxygen precipitates, A-defects and other dislocation related defects similar to A-defects (e.g., stacking faults, OISF, and slip defects), and DSODs.

According to the method of the present invention, a surface of a semiconductor substrate is etched by a gaseous etchant in a reducing atmosphere to delineate or decorate grown-in-defects in the surface of the semiconductor substrate. Briefly, the present process involves exposing the surface of the semiconductor substrate to a reducing atmosphere comprising a gaseous etchant at a temperature and duration sufficient to etch the surface of the semiconductor silicon substrate and delineate grown-in-defects disposed in the semiconductor silicon substrate. The surface of the semiconductor silicon substrate having delineated grown-in-defects thereon is then scanned with an optical detection device.

The semiconductor substrate comprises a semiconductor wafer comprising two major, generally parallel surfaces, one of which is a front surface of the substrate and the other of which is a back surface of the substrate. A circumferential edge joining the front and back surfaces, and a central plane lies between the front and back surfaces. Prior to any operation as described herein, the front surface and the back surface of the substrate may be substantially identical. A surface is referred to as a "front surface" or a "back surface" merely for convenience and generally to distinguish the surface upon which the operations of method of the present invention are performed. In some embodiments of the present invention, the operations of the invention are performed on the front surface of the semiconductor substrate. In some embodiments of the present invention, the operations of the present invention are performed on both the front surface and the back surface of the semiconductor substrate.

In some embodiments, the semiconductor substrate comprises a semiconductor wafer. In preferred embodiments, the semiconductor wafer comprises a material selected from the group consisting of silicon, silicon carbide, silicon germanium, silicon nitride, silicon dioxide, gallium arsenic, gallium nitride, indium phosphide, indium gallium arsenide, and germanium. The semiconductor wafer may comprise combinations of such materials, e.g., in a multilayer structure. In particularly preferred embodiments, the semiconductor wafer comprises a wafer sliced from a single crystal silicon wafer which has been sliced from a single crystal ingot grown in accordance with conventional Czochralski crystal growing methods. Such methods, as well as standard silicon slicing, lapping, etching, and polishing techniques are disclosed, for example, in F. Shimura, Semiconductor Silicon Crystal Technology, Academic Press, 1989, and Silicon Chemical Etching, (J. Grabmaier ed.) Springer-Verlag, N.Y., 1982 (incorporated herein by reference). In some preferred embodiments, the semiconductor silicon substrate is a polished silicon wafer grown by the CZ method having a nominal diameter of at least about 150 mm, at least about 200 mm, at least about 300 mm or even 450 mm. Typically, the wafer has a nominal diameter of from about 150 mm and 450 mm, more typically from about 200 mm and 450 mm or from about 300 mm to about 450 mm. In some embodiments the nominal diameter is 150 mm, 200 mm, 300 mm or 450 mm.

The method of the present invention involves steps that etch the front surface of the semiconductor substrate in order to delineate and/or decorate grown-in defects that intersect the surface or are located within a depth from the front surface up to the amount of the surface layer removed by the etch step. The etching step occurs in a reducing atmosphere comprising a gaseous etchant. The gaseous etchant includes any gaseous material capable of etching silicon and delineating the crystallographic defects. Such gaseous etchants may include, for example, hydrogen chloride, hydrogen bromide, and/or hydrogen iodide. In preferred embodiments, the gaseous etchant comprises hydrogen chloride. In preferred embodiments, the etching occurs at elevated temperatures.

The etching step of the semiconductor substrate may occur in a reactor that is capable of achieving temperatures up to about 1100° C., such as between about 850° C. and about 1100° C., preferably between about 900° C. and about 1100° C. Additionally, the reactor comprises a gas inlet and a gas outlet, the gas inlet being capable of adjusting the ambient atmosphere inside the reactor chamber. In some embodiments of the method, the reactor suitable for carrying out the method of the present invention is an epitaxial reactor. In some embodiments, therefore, the semiconductor substrate may be loaded into the chamber of an epitaxial reactor. An exemplary epitaxial reactor suitable for the process of the present invention is an epsilon E3000 single-wafer epitaxial reaction manufactured by ASM International. Other reactor chambers include those marketed under the trade name Centura by Applied Materials.

According to the method of the present invention, the semiconductor substrate is exposed to a reducing atmosphere. In preferred embodiments of the present invention, the reducing atmosphere comprises $H_2$. The reducing atmosphere is suitable for removing oxide from the wafer surface so that hydrogen chloride may react with the wafer surface. Advantageously, the reducing atmosphere may also smooth the wafer surface.

In some embodiments of the method of the present invention, the semiconductor substrate is heated during exposure to a reducing atmosphere. In some embodiments, the temperature of the reactor may be increased prior to exposure to the reducing atmosphere. In some embodiments, the temperature may be increased after the reducing atmosphere is introduced into the reactor. Generally, the semiconductor silicon substrate is heated to a temperature of at least about 850° C., typically at least about 900° C. and held at that temperature for a duration from about 5 seconds to about 180 seconds, such as from about 5 seconds to about 120 seconds, preferably from about 15 seconds to about 60 seconds, such as about 30 seconds. Pre-heating is preferably at a duration sufficient to remove oxide from the silicon surface. Preferably, the semiconductor silicon substrate is heated to a temperature of from about 900° C. to about 1250° C., such as from about 900° C. to about 1100° C., and more preferably to a temperature of about 1100° C., for a period of about 30 seconds.

After holding the semiconductor substrate at elevated temperatures, in some embodiments, the temperature is decreased to a temperature between about 800° C. to about 1100° C., preferably between about 900° C. to about 1050° C. In a preferred embodiment, the temperature is decreased to 1000° C. The temperature decrease occurs since the etch step is temperature sensitive for a given etchant concentration.

Prior to or upon reaching the desired temperature in the reactor chamber, a gaseous etchant is introduced into the reducing atmosphere. In preferred embodiments, the gaseous etchant comprises hydrogen chloride, which is introduced into the $H_2$ flow to achieve a desired HCl concentration. Preferably, the HCl flow rate is adjusted to achieve an HCl concentration between about 0.05 volume % to about 5 volume %, such as between about 0.25 volume % to about 1.5 volume %, or between about 0.25 volume % to about 1 volume %. The semiconductor silicon substrate is then held at the lowered temperature in the reducing atmosphere comprising gaseous acid for a duration sufficient to decorate the grown-in-defects so that they are capable of being detected by an optical detection device. In general, such durations may range from about 30 seconds to about 300 seconds. Exposure of the semiconductor substrate to the reducing atmosphere comprising a gaseous acid generally etches the surface of the substrate at an etch rate between about 1 Angstrom/second and about 20 Angstrom/second, preferably between about 3 Angstrom/second and about 10 Angstrom/second. The entire surface is etched by the etching process, and defects are preferentially etched.

In one preferred embodiment, a semiconductor silicon substrate is held in a reducing atmosphere comprising hydrogen and gaseous HCl at a concentration of 0.5% at a temperature of about 1000° C. The duration depends upon the temperature and etch rate, which is a function of the hydrogen chloride concentration. Etching generally occurs until between about 500 Angstroms and about 1500 Angstroms of surface are etched, preferably between about 700 Angstroms and about 1000 Angstroms. Empirical results obtained to date have shown that at a given temperature, the etch becomes more decorating for a higher HCl concentration (higher etch rate). At a given HCl concentration lower temperature tends to make the etch more decorating.

After the etch, the temperature of the semiconductor substrate is decreased to a temperature of from about 700° C. to about 950° C., preferably from about 700° C. to about 900° C. so that the substrate may be more easily and safely handled.

In some embodiments of the process of the present invention, the semiconductor substrate is subjected to a thermal cycle prior to being contacted with the gaseous etchant. This thermal cycle could be a stand alone thermal cycle. This thermal cycle allows defects present in the semiconductor silicon substrate to become more detectable prior to the defects being processed by the HCl etch, e.g., via growing defects, in particular oxygen precipitates, A defects, and B defects, and the like. The thermal cycle temperature generally exceeds about 800° C. since oxygen precipitates generally grow too slowly for commercially practicable purposes at temperatures less than about 800° C. In general, the maximum temperature of anneal is limited by the oxygen solubility in silicon. That is, the maximum temperature is preferably kept below the temperature at which oxygen precipitates begin to dissolve in the silicon wafer material. Accordingly, the anneal temperature may be as high as 1150° C. for wafers having relatively high oxygen concentration, and is generally lower, such as 1125° C. or even 1100° C., for wafers having lower oxygen concentrations. In view thereof, the anneal temperature is generally between about 800° C. and about 1150° C., preferably between about 800° C. and about 1125° C., or between about 800° C. and about 1100° C., or between about 900° C. and about 1050° C., or even between about 900° C. and about 1000° C. The growth rate of defects, e.g., oxygen precipitates, depends upon the anneal temperature and oxygen concentration of the wafer. Low temperature anneals sufficient to grow defects such as oxygen precipitates, are generally at least about 2 hours, such as between about 2 hours and about 20 hours. High temperature anneals may be shorter, such as between about 30 minutes and about 16 hours. Annealing may occur at multiple temperatures, which may be achieved via ramped or stepped profiles. The thermal cycle may occur within the context of conventional wafer processing, e.g., an NEC1 to grow oxygen precipitates or DRAM thermal cycle. A specific NEC1 cycle comprises anneal at 800° C. for 4 hours followed by 1000° C. for 16 hours.

Once the semiconductor substrate has been cooled to a temperature sufficient to permit handling, the semiconductor substrate is removed from the reactor. In the next step of the present invention, the surface of the semiconductor silicon substrate is scanned to determine the number and type of surface defects. In some embodiments, the surface of the semiconductor substrate may be scanned with an optical detection device. Suitable devices include the Surfscan SP1$^{DLS}$, SP2, and SP3, all manufactured by KLA-Tencor. The process of the present invention is capable of decorating grown-in-defects such that they become easily detectable by such optical detection instruments. Defects may become more easily detectable either by removal of silicon from around the defect thereby exposing it so it can scatter light directly or by creating a faceted pit around the defect, which can scatter light making it detectable. Current results to date have shown that faceted pit formation is the dominant mechanism by which the defects are made detectable.

The method of the present invention is capable of detecting defects that were previously undetectable via conventional methods. For example, it may be possible to detect oxygen precipitates of less than 20 nm in diameter. Additionally, by scanning the surface of the semiconductor silicon substrate, it is possible to classify the defects present on the surface of the semiconductor silicon substrate. For example, for a given etch rate and etch duration, different types of defects scatter into different latex sphere equivalent (LSE) size bins. Current empirical results obtained to date have shown, for example, that very small vacancy agglomerates scatter in 0.16-0.2 micrometer LSE bins after etch while oxygen precipitates typically fall in 0.12- 0.14 micrometer bin size. A-defects for the same etch fall in the 0.14-0.16 micrometer size range. In view thereof, size provides a reliable indication of the type of defects in the wafer. Defects may also be classified based on the wide/narrow scattering ratios.

Defect classification may also be confirmed by microscopes, such a SEMs, Atomic Force Microscopes, and Interference Differential Contrast Optical Microscopes.

Further, by establishing a process by which defects may be detected and classified, wafers can more easily be sorted according to the type, concentration, and size of the defects present on the surfaces of such wafers. Such a process would enable an efficient method of determining a suitable purpose for each wafer.

EXAMPLE 1

A polished silicon p-type (boron) wafer was grown by the CZ method to be vacancy dominant (A Perfect Silicon™ prepared by MEMC Electronic Materials). The wafer was free of COP and FPD defects. The oxygen concentration was about 9 ppma. The wafer diameter was 300 mm and thickness was about 775 angstrom. The resistivity was between 5-20 ohm cm. The wafer was polished by a chemical-mechanical polishing step followed by industry standard SC1, SC2 cleaning The cleaned wafer was inspected on SP2 and subjected to a thermal cycle in a 300 mm Centura epi reactor manufactured by Applied Materials. The wafer was loaded into the process chamber, subjected to 30s $H_2$ bake at temperature of 1130° C. The temperature was lowered to 1000° C. and HCl gas was injected into the $H_2$ stream to achieve a concentration of 1%. The wafer was held at this temperature in this HCl/$H_2$ mixture for a time of 100s during which time approximately 1000 angstroms of SI was etched from the surface. The HCl was turned off and the temperature lowered to 900° C. and the wafer was unloaded from the process chamber.

The wafer was inspected on a SP1 DLS inspection tool in darkfield normal incidence mode. The post HCl etch inspection showed a high density of LPD counts in the center of the wafer with total>0.12 um LPD count of 1469.

Figure 1B:
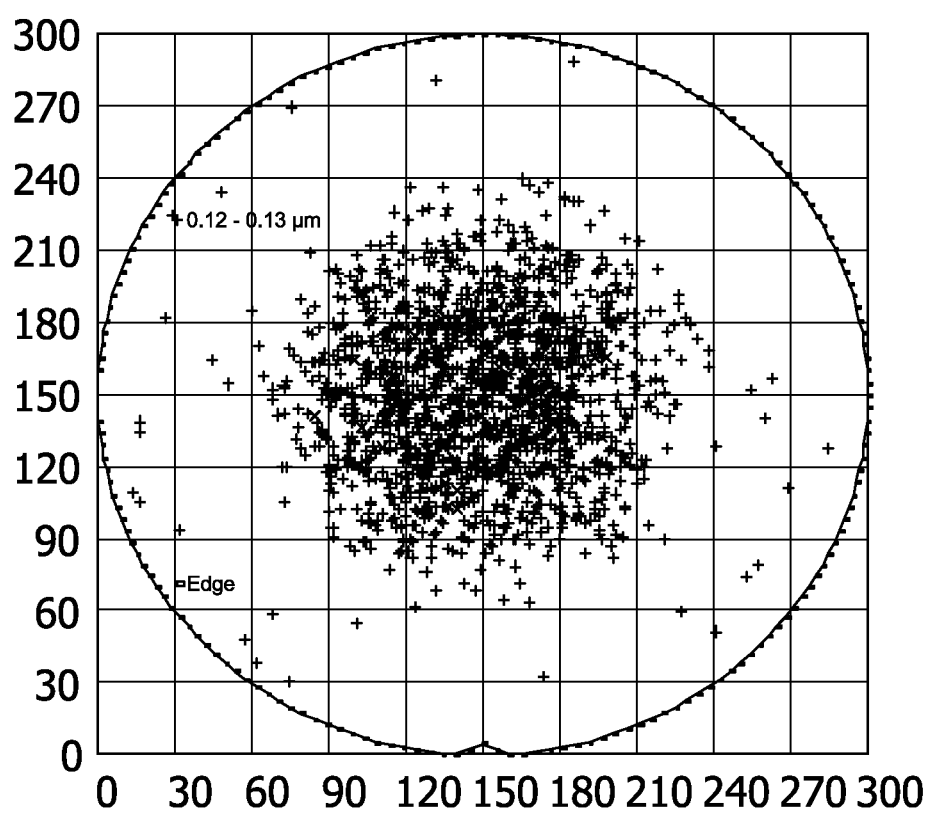

FIGS. 1A and 1B are illustrations of the location of oxygen precipitates that are present on the surface of a polished silicon wafer. FIG. 1A illustrates oxygen precipitates in the polished wafer prior to HCl decorating. FIG. 1B illustrates oxygen precipitates on the wafer surface that has been treated by the process described above. As can be seen from FIG. 1B, by using the process described above on this particular wafer, it was able to be determined that this wafer included a heavy oxygen precipitation core.

EXAMPLE 2

Two polished silicon p-type (boron) wafers were grown by the CZ method to be vacancy dominant (A Perfect Silicon™ prepared by MEMC Electronic Materials). The wafer were sliced adjacent from each other from the same ingot. The wafers were free of COP and FPD defects. The oxygen concentration was about 9 ppma. The wafers had diameters of 300 mm and thicknesses of about 775 angstrom. The resistivity was between 5-20 ohm cm. Prior to polishing, one of the wafers was subjected to a 15 hour anneal at 800° C. The second wafer was not annealed. The wafers were polished by a chemical-mechanical polishing step followed by industry standard SC1, SC2 cleaning The cleaned wafers were inspected on SP2 and subjected to a thermal cycle in a 300 mm Centura epi reactor manufactured by Applied Materials. The wafers were loaded into the process chamber, subjected to 30s $H_2$ bake at temperature of 1130° C. The temperature was lowered to 1000° C. and HCl gas was injected into the $H_2$ stream to achieve a concentration of 1%. The wafers were held at this temperature in this HCl/$H_2$ mixture for a time of 100s during which time approximately 1000 angstroms of SI was etched from the surface. The HCl was turned off and the temperature lowered to 900° C., and the wafers were unloaded from the process chamber.

Figure 2C:
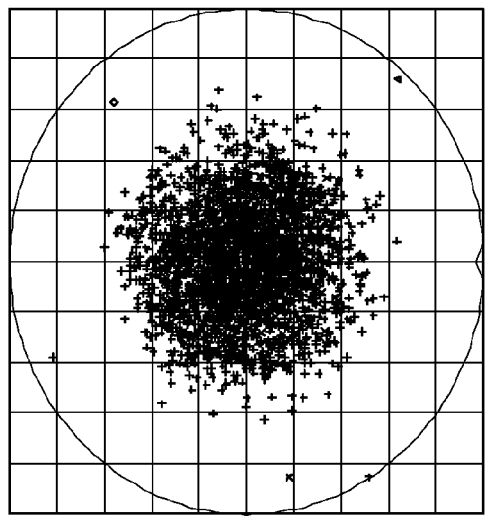
FIG. 2 is a map of interstitial defects (the band) and oxygen precipitates (in the center) on the surface of a wafer, wherein the interstitial defects and oxygen precipitates have been delineated by the process of the present invention.
Figure 2B:
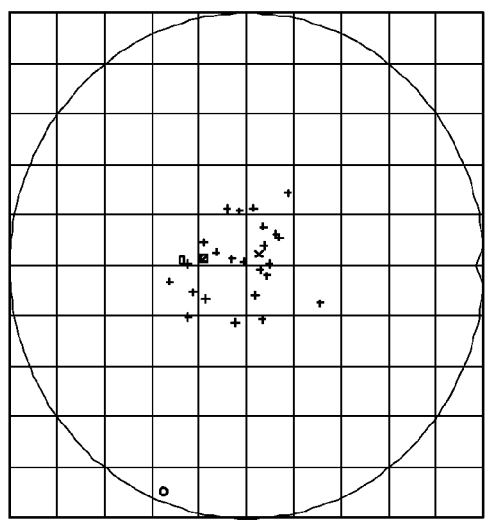
Figure 2A:
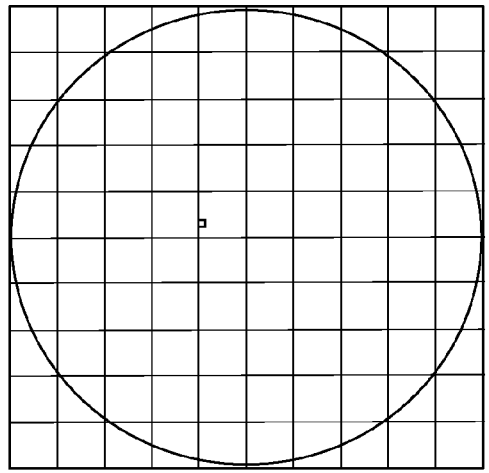

The wafers were inspected on a SP1 DLS inspection tool in darkfield normal incidence mode for LPD. FIGS. 2A, 2B, and 2C are illustrations of the location of oxygen precipitates that are present on the surface of a polished silicon wafer. FIG. 2A shows the defects and particles detected on the un-annealed wafer prior to HCl decorating. No crystal related defect patterns were detected only a few randomly located particles. FIG. 2B illustrates oxygen precipitates on the same wafer surface that had been treated by the HCl etch process described above. As can be seen from FIG. 2B, by using the process described above on this un-annealed wafer, oxygen precipitates were detected in a small region near the wafer center. FIG. 2C illustrates oxygen precipitates on the wafer surface of the annealed wafer that had been HCl treated by the process described above. As can be seen from FIG. 2C, by using the process described above on an annealed wafer, it was able to be determined that this wafer included a heavy oxygen precipitation core.

EXAMPLE 3

A polished silicon p-type (boron) wafer was grown by the CZ method. The ingot was grown to produce a vacancy dominated vacancy region in the center of the wafer surrounded by an interstitial dominated region in which A-defects were formed. Prior to polishing, the wafer was subjected to a 65 minute, 930° C. anneal. The wafer was polished by a chemical-mechanical polishing step followed by industry standard SC1, Sc2 cleaning The cleaned wafer was inspected on SP2 and subjected to a thermal cycle in a 300 mm Centura epi reactor manufactured by Applied Materials. The wafer was loaded into the process chamber, subjected to 30s $H_2$ bake at temperature of 1130° C. The temperature was lowered to 1000° C. and HCl gas was injected into the $H_2$ stream to achieve a concentration of 1%. The wafer was held at this temperature in this HCl/$H_2$ mixture for a time of 100s during which time approximately 1000 angstroms of SI was etched from the surface. The HCl was turned off and the temperature lowered to 900° C. and the wafer was unloaded from the process chamber.

The wafer was inspected on a SP1 DLS inspection tool in darkfield normal incidence mode. Post HCl etch inspection revealed the presence of a band of LPD defects along with a region of smaller sized region LPDs in the wafer center. The total LPD count>0.12 um in this case is 1480.

Figure 3:
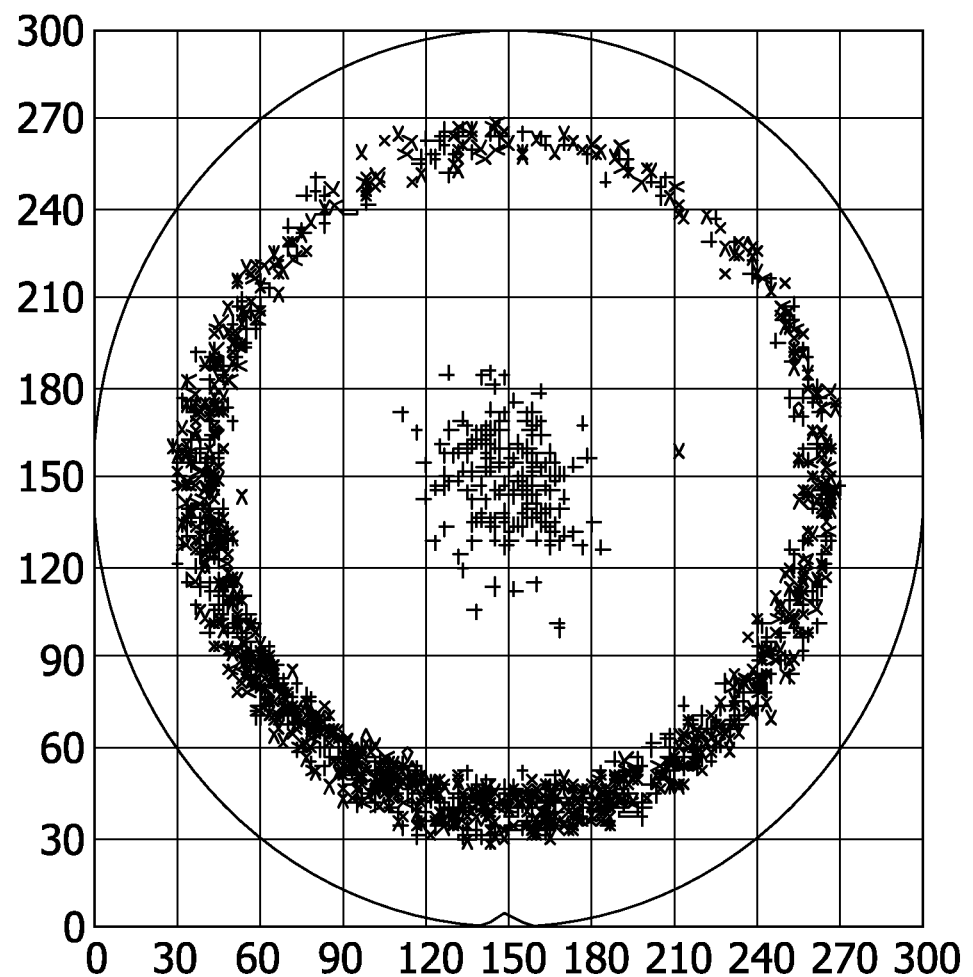
FIG. 3 is a map of low density oxygen precipitates at the edge of a wafer, wherein the low density oxygen precipitates have been delineated by the process of the present invention.

FIG. 3 illustrates the location of interstitial defects and oxygen precipitates that are present on the surface of a polished silicon wafer that has been treated by the process described above. As can be seen from FIG. 3, by using the process described above on this particular wafer, it was able to be determined that this wafer included both an interstitial band and an oxygen precipitate core.

EXAMPLE 4

A polished silicon p-type (boron) wafer was grown by the CZ method to be vacancy dominant (A Perfect Silicon™ prepared by MEMC Electronic Materials). The wafer was free of COP and FPD defects. The oxygen concentration was about 9-ppma. The wafer diameter was 300 mm and thickness was about 775 angstrom. The resistivity was between 5-20 ohm cm. Prior to polishing, the wafer was subjected to a 65 minute, 930° C. anneal. The wafer was polished by a chemical-mechanical polishing step followed by industry standard SC1, Sc2 cleaning The cleaned wafer was inspected on SP2 and subjected to a thermal cycle in a 300 mm Centura epi reactor manufactured by Applied Materials. The wafer was loaded into the process chamber, subjected to 30s $H_2$ bake at temperature of 1130° C. The temperature was lowered to 1000° C. and HCl gas was injected into the $H_2$ stream to achieve a concentration of 1%. The wafer was held at this temperature in this HCl/$H_2$ mixture for a time of 100s during which time approximately 1000 angstroms of SI was etched from the surface. The HCl was turned off and the temperature lowered to 900° C. and the wafer was unloaded from the process chamber.

The wafer was inspected on a SP1 DLS inspection tool in darkfield normal incidence mode. Post HCl etch inspection revealed a low density band of defects in the outer edge of the wafer. The total LPD count>0.12 um in the band is 130.

Figure 4:
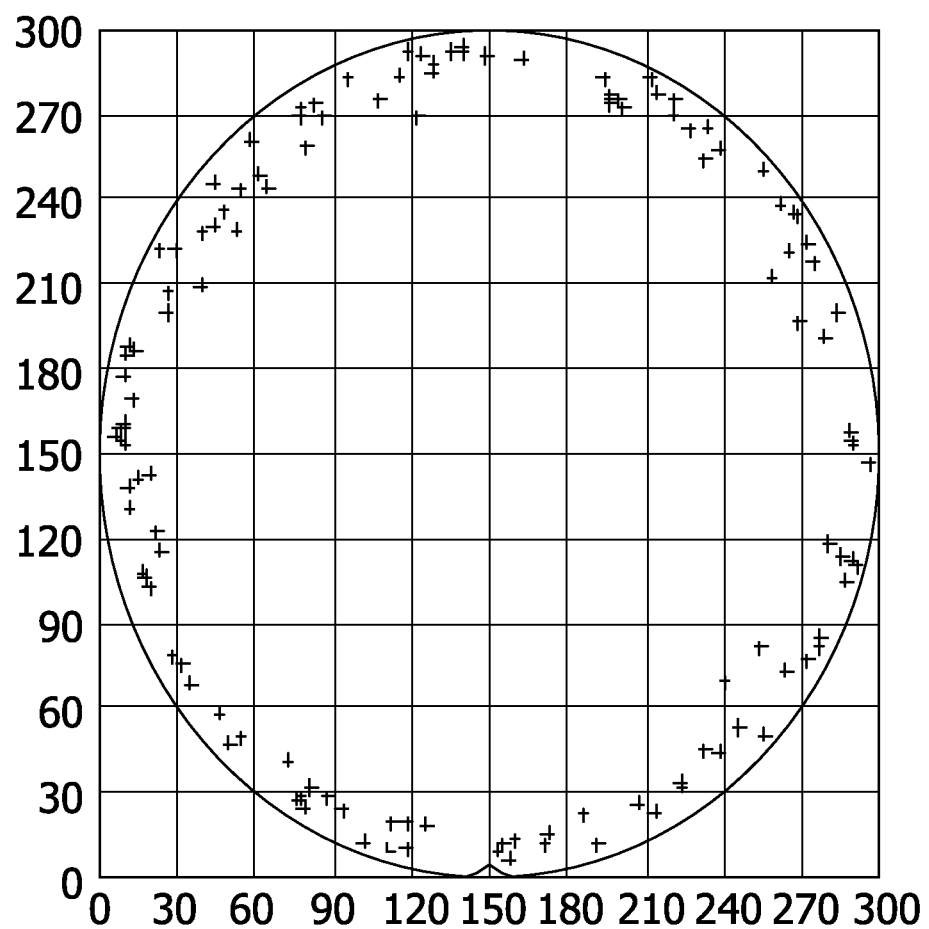
FIG. 4 is a map of interstitial defects on the surface of a wafer, wherein the interstitial defects have been delineated by the process of the present invention.

FIG. 4 illustrates the location of low density oxygen precipitates that are present on the surface of a polished silicon wafer that has been treated by the process described above. As can be seen from FIG. 4, by using the process described above on this particular wafer, it was able to be determined that this wafer included a low density oxygen precipitate band.

EXAMPLE 5

A silicon p-type (boron) wafer was grown by the CZ method. The ingot was grown to produce a vacancy dominated vacancy region in the center of the wafer surrounded by an interstitial dominated region in which A-defects were formed. The wafer was processed through a chemical etch to remove physical damage to the wafer surface. The wafer was cleaned using industry standard SC1, SC2 cleans. The wafer was subjected to a 65 minute, 930° C. thermal cycle after which the wafer was polished and re-cleaned following semiconductor standard methods.

The wafer was loaded into an epsilon E3000 reactor, manufactured by ASM International. The wafer was heated in a $H_2$ gas ambient atmosphere at atmospheric pressure and a flow rate of about 80 standard liters per minute (slm). The temperature of hydrogen gas exposure was about 1100° C. for duration of about 30 seconds. The temperature was then lowered to about 1000° C. Hydrogen chloride gas (HCl) was introduced at a flow rate of about 0.4 slm into the $H_2$ flow to achieve an HCl concentration of about 0.5%. The wafer was held at this temperature and flow for approximately 160 seconds. Holding the wafer at this temperature and ambient atmosphere resulted in an etch removal of about 550 angstroms for an etch rate of about 3.4 angstroms/second. The temperature was ramped down to about 700-900° C.

The wafer was inspected on a SP1 DLS inspection tool in darkfield normal incidence mode. Post HCl inspection revealed a band of defects corresponding to the A-defect band with a total LPD count of 1099 LPDs with LSE>0.12 um.

Figure 5:
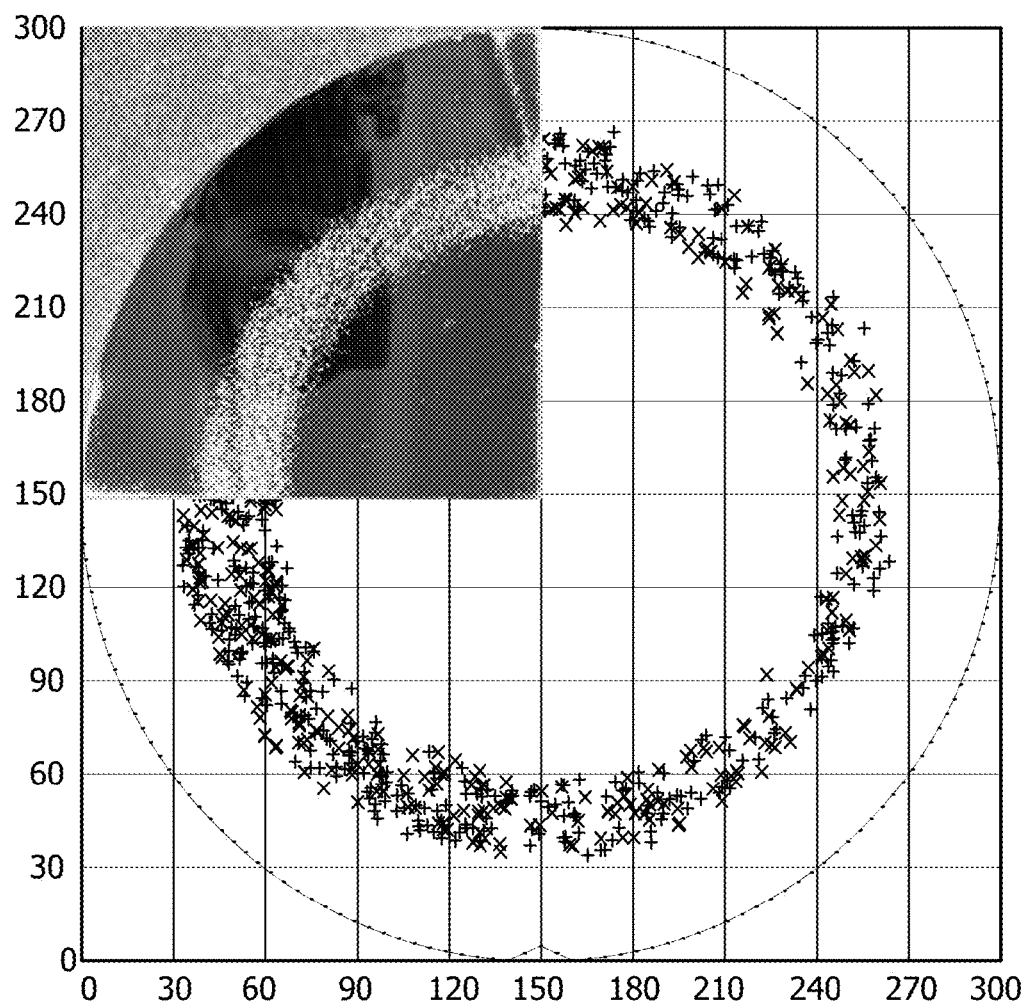
FIG. 5 is a map of DSODs on the surface of a wafer, wherein the DSODs have been delineated by the process of the instant invention.

FIG. 5 illustrates the location of interstitial defects that are present on the surface of a polished silicon wafer that has been treated by the process described above. As can be seen from FIG. 5, by using the process described above on this particular wafer, it was able to be determined that this wafer included an interstitial band only. The upper left quadrant of FIG. 5 illustrates the defects via copper decoration.

EXAMPLE 6

A polished silicon p-type (boron) wafer was grown by the CZ method to be very slightly vacancy dominant (A Perfect Silicon™ prepared by MEMC Electronic Materials). This wafer contained a "DSOD" core in the wafer center. The core was believed to very small vacancy agglomerates not large enough to be detected by typical tests for COPs such as FPD.

The wafer was loaded into an epsilon E3000 reactor, manufactured by ASM International. The wafer was heated in a $H_2$ gas ambient atmosphere at atmospheric pressure and a flow rate of about 80 standard liters per minute (slm). the temperature of hydrogen gas exposure was about 1100° C. for duration of about 30 seconds. The temperature was then lowered to about 1000° C. Hydrogen chloride gas (HCl) was introduced at a flow rate of about 0.4 slm into the $H_2$ flow to achieve an HCl concentration of about 0.5%. The wafer was held at this temperature and flow for approximately 160 seconds. Holding the wafer at this temperature and ambient atmosphere resulted in an etch removal of about 550 angstroms for an etch rate of about 3.4 angstroms/second. The temperature was ramped down to about 700-900° C.

The wafer was inspected on a SP1 TBI inspection tool in darkfield normal incidence mode. In this case the LPD inspection was limited to LPDs with LSE size>0.16 um rather than the usual 0.12 um threshold. This enabled distinguishing between these defects and typical oxygen precipitates which are detected at the 0.12 um LPD size. The post HCl etch inspection showed well defined region at the center of the wafer with LPD s in bin sizes>0.16 um.

Figure 6:
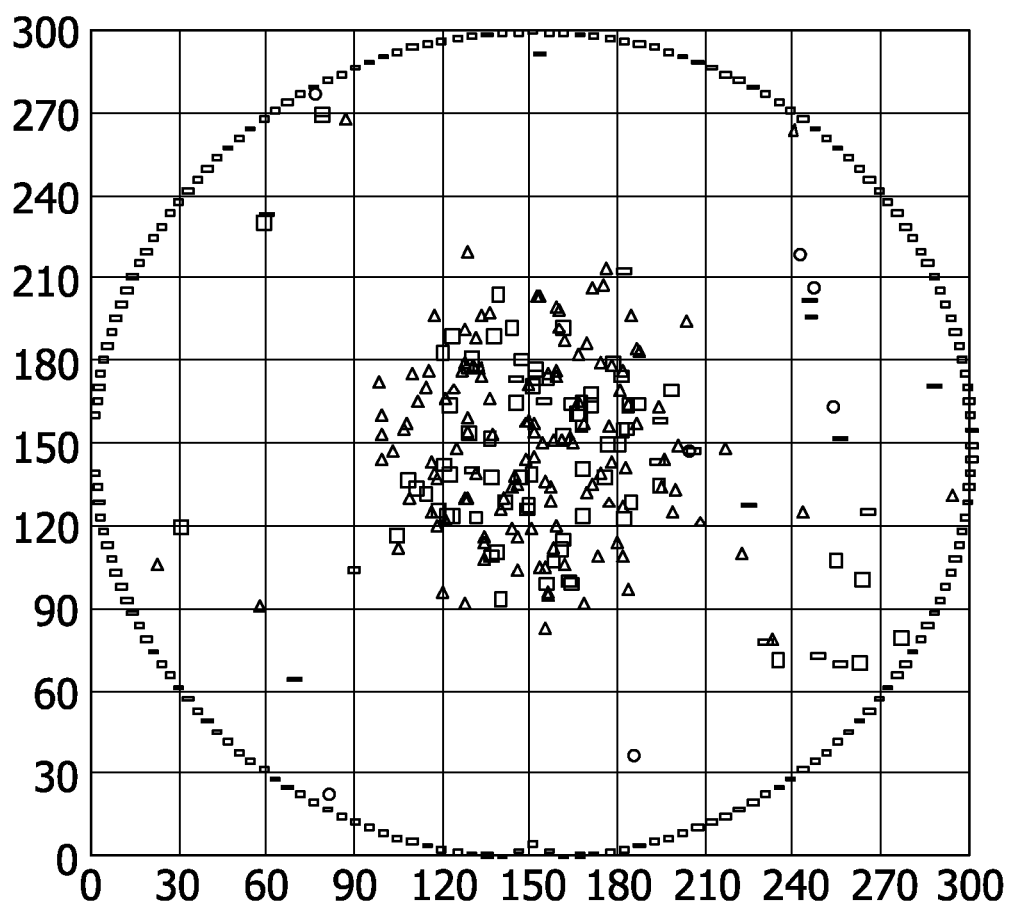

FIG. 6 illustrates the location of DSODs on the surface of a polished silicon wafer that has been treated by the process described above. As can be seen from FIG. 6, by using the process described above on this particular wafer, it was able to be determined that this wafer included a DSOD core.

In view of the above, it will be seen that the several objects of the invention are achieved. As various changes could be made in the above-described process without departing from the scope of the invention, it is intended that all matters contained in the above description be interpreted as illustrative and not in a limiting sense. In addition, when introducing elements of the present invention or the preferred embodiment(s) thereof, the articles "a," "an," "the" and "said" are intended to mean that there are one or more of the elements. The terms "comprising," "including" and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for detecting grown-in-defects in a surface of a semiconductor substrate, said method comprising:
   exposing the surface of the semiconductor substrate to a first reducing atmosphere comprising hydrogen at a first temperature between about 900° C. and about 1250° C. for a duration sufficient to remove oxide from the surface of the semiconductor substrate;
   exposing the surface of the semiconductor substrate to a second reducing atmosphere comprising hydrogen and a gaseous etchant selected from the group consisting of hydrogen chloride, hydrogen bromide, hydrogen iodide, and combinations thereof at a second temperature between about 800° C. and about 1100° C. for a duration sufficient to etch the surface of the semiconductor substrate and delineate grown-in-defects disposed in the semiconductor substrate, wherein the second temperature is lower than the first temperature; and scanning the surface of the semiconductor substrate having delineated grown-in-defects thereon with an optical detection device.

2. The method of claim 1 wherein the semiconductor substrate comprises a semiconductor wafer comprising two major, generally parallel surfaces, one of which is a front surface of the substrate and the other of which is a back surface of the substrate, a circumferential edge joining the front and back surfaces, and a central plane between the front and back surfaces.

3. The method of claim 2 wherein the semiconductor wafer comprises a material selected from the group consisting of silicon, silicon carbide, silicon germanium, silicon nitride, silicon dioxide, gallium arsenic, gallium nitride, indium phosphide, indium gallium arsenide, germanium, and combinations thereof.

4. The method of claim 2 wherein the semiconductor wafer comprises a wafer sliced from a single crystal silicon ingot grown by the Czochralski method.

5. The method of claim 1 wherein the grown-in-defects are selected from the group consisting of COPs, oxygen precipitates, A-defects, and DSODs.

6. The method of claim 1 wherein the second reducing atmosphere comprises hydrogen and gaseous hydrogen chloride at a concentration between about 0.05% and about 5%.

7. The method of claim 1 wherein the second reducing atmosphere comprises hydrogen and the gaseous hydrogen chloride at a concentration between about 0.25% and about 1%.

8. The method of claim 1 wherein the second temperature is between about 900° C. to about 1050° C.

9. The method of claim 1 wherein the method further comprises subjecting the semiconductor substrate to a thermal cycle prior to exposing the surface of the semiconductor substrate to the first reducing atmosphere, wherein the thermal cycle comprises heating the semiconductor substrate to a third temperature between about 800° C. and about 1150° C. for at least 2 hours.

10. The method of claim 9 wherein the third temperature is between about 900° C. and about 1000° C., and the duration of the thermal cycle is between 2hours and about 20 hours.

11. A method of sorting a plurality of semiconductor wafers, said method comprising:

exposing the surface of the semiconductor substrate to a first reducing atmosphere comprising hydrogen at a first temperature between about 900° C. and about 1250° C. for a duration sufficient to remove oxide from the surface of the semiconductor substrate;

exposing the plurality of semiconductor wafers to a second reducing atmosphere comprising hydrogen and a gaseous etchant selected from the group consisting of hydrogen chloride, hydrogen bromide, hydrogen iodide, and combinations thereof at a second temperature between about 800° C. and about 1100° C. for a duration sufficient to etch the surface of the plurality of semiconductor substrates and delineate grown-in-defects disposed in the plurality of semiconductor substrates, wherein the second temperature is lower than the first temperature;

scanning the surface of the wafers with an optical detection device for the delineated grown-in-defects; and sorting the wafers based on the type, concentration, and size of the defects detected.

* * * * *